US00PP25230P2

(12) United States Plant Patent
Schaber

(10) Patent No.: US PP25,230 P2
(45) Date of Patent: Jan. 13, 2015

(54) GERANIUM PLANT NAMED 'OGLGER6132'

(50) Latin Name: *Pelargonium×hortorum*
Varietal Denomination: Oglger6132

(71) Applicant: Margaret Schaber, Encinitas, CA (US)

(72) Inventor: Margaret Schaber, Encinitas, CA (US)

(73) Assignee: ECKE Ranch B.V., De Lier (NL)

( * ) Notice: Subject to any disclaimer, the term of this patent is extended or adjusted under 35 U.S.C. 154(b) by 87 days.

(21) Appl. No.: 13/815,475

(22) Filed: Mar. 5, 2013

(51) Int. Cl.
*A01H 5/00* (2006.01)

(52) U.S. Cl.
USPC ..... Plt./325

(58) Field of Classification Search
USPC ..... Plt./325
See application file for complete search history.

*Primary Examiner* — Annette Para
(74) *Attorney, Agent, or Firm* — C. A. Whealy

(57) ABSTRACT

A new and distinct cultivar of Zonal Geranium plant named 'Oglger6132', characterized by its upright to outwardly spreading and mounded plant habit; moderately vigorous growth habit; freely branching habit; dark green-colored leaves; freely flowering habit; and dark red-colored flowers arranged in umbels held above and beyond the foliar plane on strong peduncles.

1 Drawing Sheet

Botanical designation: *Pelargonium×hortorum*.
Cultivar denomination: 'OGLGER6132'.

BACKGROUND OF THE INVENTION

The present invention relates to a new and distinct cultivar of Zonal Geranium plant, botanically known as *Pelargonium×hortorum*, and hereinafter referred to by the name 'Oglger6132'.

The new Zonal Geranium plant is a product of a planned breeding program conducted by the Inventor in Lompoc, Calif. The objective of the breeding program is to create new Zonal Geranium plants with attractive leaf and flower coloration and good garden performance.

The new Zonal Geranium plant originated from a cross-pollination made by the Inventor in January, 2005 in Lompoc, Calif. of *Pelargonium×hortorum* 'Candy Cardinal', disclosed in U.S. Plant Pat. No. 14,114, as the female, or seed, parent with a proprietary selection of *Pelargonium×hortorum* identified as code number 12816-1, not patented, as the male, or pollen, parent. The new Zonal Geranium plant was discovered and selected by the Inventor as a single flowering plant from within the progeny of the stated cross-pollination in a controlled greenhouse environment in Lompoc, Calif. in August, 2005.

Asexual reproduction of the new Zonal Geranium plant by vegetative cuttings in a controlled greenhouse environment in Connellsville, Pa. since April, 2006, has shown that the unique features of this new Zonal Geranium plant are stable and reproduced true to type in successive generations.

SUMMARY OF THE INVENTION

Plants of the new Zonal Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Oglger6132'.

These characteristics in combination distinguish 'Oglger6132' as a new and distinct Zonal Geranium plant:

1. Upright to outwardly spreading and mounded plant habit.
2. Moderately vigorous growth habit.
3. Freely branching habit.
4. Dark green-colored leaves.
5. Freely flowering habit.
6. Dark red-colored flowers arranged in umbels held above and beyond the foliar plane on strong peduncles.

Plants of the new Zonal Geranium differ primarily from plants of the female parent, 'Candy Cardinal', in plant and growth habit as plants of the new Zonal Geranium are more vigorous and larger than plants of 'Candy Cardinal'. Plants of the new Zonal Geranium and 'Candy Cardinal' also differ slightly in leaf and flower color.

Plants of the new Zonal Geranium differ primarily from plants of the male parent selection in leaf and flower color as plants of the male parent selection have darker green-colored leaves and less intense dark red-colored flowers.

Plants of the new Zonal Geranium can be compared to plants of *Pelargonium×hortorum* 'Oglger14007', disclosed in U.S. Plant Pat. No. 21,230. In side-by-side comparisons conducted in Encinitas, Calif., plants of the new Zonal Geranium differed primarily from plants of 'Oglger14007' in growth habit as plants of the new Zonal Geranium were not as vigorous as plants of 'Oglger14007'. In addition, plants of the new Zonal Geranium had darker red-colored flowers than plants of 'Oglger14007'.

BRIEF DESCRIPTION OF THE PHOTOGRAPHS

The accompanying colored photographs illustrate the overall appearance of the new Zonal Geranium plant showing the colors as true as it is reasonably possible to obtain in colored reproductions of this type. Colors in the photographs may differ slightly from the color values cited in the detailed botanical description which accurately describe the colors of the new Zonal Geranium plant.

The photograph at the bottom of the sheet comprises a side perspective view of a typical flowering plant of 'Oglger6132' grown in a container.

The photograph at the top of the sheet is a close-up view of a typical flowering plant of 'Oglger6132 '.

DETAILED BOTANICAL DESCRIPTION

The aforementioned photographs and following observations, measurements and values describe plants grown during the early spring in 16.5-cm containers in a polyethylene-covered greenhouse in Encinitas, Calif. and under cultural conditions which closely approximate Zonal Geranium commercial production. During the production of the plants, day temperatures averaged 27° C., night temperatures averaged 18° C. and light levels averaged 4,000 foot-candles. Plants were 17 weeks old when the photographs and the description were taken. In the detailed description, color references are made to The Royal Horticultural Society Colour Chart, 2007 Edition, except where general terms of ordinary dictionary significance are used.

Botanical classification: *Pelargonium×hortorum* 'Oglger6132'.

Parentage:

*Female, or seed, parent.*—*Pelargonium×hortorum* 'Candy Cardinal', disclosed in U.S. Plant Pat. No. 14,114.

*Male or pollen parent.*—Proprietary selection of *Pelargonium×hortorum* identified as code number 12816-1, not patented.

Propagation:

*Type.*—By vegetative cuttings.

*Time to initiate roots, summer.*—About ten days at temperatures about 20° C.

*Time to initiate roots, winter.*—About two weeks at temperatures about of 16° C.

*Time to produce a rooted young plant, summer.*—About four weeks at temperatures about 20° C.

*Time to produce a rooted young plant, winter.*—About four weeks at temperatures about 16° C.

*Root description.*—Fine, fibrous; white in color.

*Rooting habit.*—Freely branching; dense.

Plant description:

*Plant and growth habit.*—Upright to outwardly spreading and mounding plant habit; moderately vigorous growth habit.

*Branching habit.*—Freely branching habit with about seven primary lateral branches developing per plant, each primary lateral branch with secondary lateral branches; dense and bushy appearance; pinching enhances lateral branch development.

*Plant height, to top of umbels.*—About 30 cm.

*Plant height, to top of foliar plane.*—About 24.5 cm.

*Plant diameter (spread).*—About 34 cm by 43 cm.

*Lateral branches.*—Length: About 20 cm. Diameter: About 1 cm. Internode length: About 2.4 cm. Texture: Pubescent; minute. Strength: Strong. Color: Close to 146C.

Foliage description:

*Arrangement.*—Alternate; simple.

*Length.*—About 6.2 cm.

*Width.*—About 7.6 cm.

*Shape.*—Reniform.

*Apex.*—Rounded.

*Base.*—Roughly cordate.

*Margin.*—Crenate.

*Venation pattern.*—Palmate, reticulate.

*Texture, upper and lower surfaces.*—Pubescent, minute.

*Color.*—Developing leaves, upper and lower surfaces: Close to 146B. Fully expanded leaves, upper surface: Close to 147A; venation, close to 137A; no discernible zonation pattern. Fully expanded leaves, lower surface: Close to 147B; venation, close to 146A.

*Petiole.*—Length: About 5.3 cm. Diameter: About 3 mm. Texture, upper and lower surfaces: Pubescent. Color, upper and lower surfaces: Close to 147B.

Flower description:

*Flower arrangement.*—Round semi-double flowers arranged in large hemispherical to nearly spherical umbels arising from apical leaf axils; umbels displayed above and beyond the foliar plane on strong peduncles; umbels mostly upright and flowers face upright or outwardly.

*Fragrance.*—None detected.

*Quantity of flowers.*—Freely flowering habit; about 44 flowers per umbel and about 14 umbels per plant at one time.

*Flowering season.*—In California, flowering is continuous during the spring and summer.

*Flower longevity.*—Individual flowers last about five to seven days on the plant; flowers persistent.

*Umbel height.*—About 8.8 cm.

*Umbel diameter.*—About 11.2 cm.

*Flower diameter.*—About 4.1 cm.

*Flower depth (height).*—About 2.2 cm.

*Flower buds.*—Length: About 1.6 cm. Diameter: About 1.2 cm. Shape: Oval. Color: Close to 46A.

*Petals.*—Quantity per flower and arrangement: Typically 14 to 16 arranged in two to three whorls. Length: About 2.1 cm. Width: About 1.8 cm. Shape: Obovate. Apex: Rounded. Base: Acute. Margin: Entire. Texture, upper and lower surfaces: Smooth, glabrous; velvety. Color: When opening, upper surface: Close to 53A. When opening, lower surface: Close to 53B to 53C. Fully opened, upper surface: Close to 46A; towards the base of outer petals, close to 44A; venation, close to 46A; color becoming closer to 46B with development. Fully opened, lower surface: Close to 53C; venation, close to 53C; color does not fade with development.

*Petaloids.*—Quantity per flower and arrangement: Typically two or three central to the whorls of petals. Length: Variable, about 1.8 cm. Width: Variable, about 5 mm. Shape: Variable, somewhat distorted, roughly lanceolate. Apex: Rounded. Base: Acute. Margin: Entire, curled. Texture, upper and lower surfaces: Smooth, glabrous; velvety. Color: When opening and fully opened, upper surface: Close to 46B. When opening and fully opened, lower surface: Close to 46D.

*Sepals.*—Quantity per flower: Typically six arranged in a single whorl. Length: About 1.1 cm. Width: About 3 mm. Shape: Narrowly elliptical. Apex: Acuminate. Base: Truncate. Margin: Entire. Texture, upper surface: Smooth, glabrous. Texture, lower surface: Pubescent. Color, upper and lower surfaces: Close to 146C.

*Peduncle (umbel stem).*—Length: About 15 cm. Diameter: About 4 mm. Angle: About 35° to 45° from stem axis. Strength: Strong. Texture: Pubescent; minute. Color: Close to 146B tinted with close to 187A.

*Pedicel* (*individual flower stem*).—Length: About 2.2 cm. Diameter: About 1 mm. Angle: About 15° to 55° from peduncle axis. Strength: Strong. Texture: Pubescent; minute. Color: Close to 183B.

*Reproductive organs*.—Androecium: Stamen quantity per flower: About five to seven; occasionally modified into petaloids. Filament length: About 7 mm. Filament color: Close to NN155D tinted with close to 60D. Anther length: About 2.5 mm. Anther shape: Oblong. Anther color: Close to 63B. Pollen amount: Scarce. Pollen color: Close to 179B. Gynoecium: Pistil quantity per flower: One. Pistil length: About 1.1 cm. Stigma shape: Five-parted, star-shaped; recurved. Stigma color: Close to 59B. Style length: About 2.5 mm. Style color: Close to 59C. Ovary color: Close to 195A.

*Seeds and fruits*.—Seed and fruit development have not been observed on plants of the new Zonal Geranium.

Disease & pest resistance: Plants of the new Zonal Geranium have not been observed to be resistant to pathogens and pests common to Zonal Geranium plants.

Temperature tolerance: Plants of the new Zonal Geranium have been observed to tolerate temperatures ranging from about 1° C. to about 35° C.

It is claimed:

1. A new and distinct Zonal Geranium plant named 'Oglger6132' as illustrated and described.

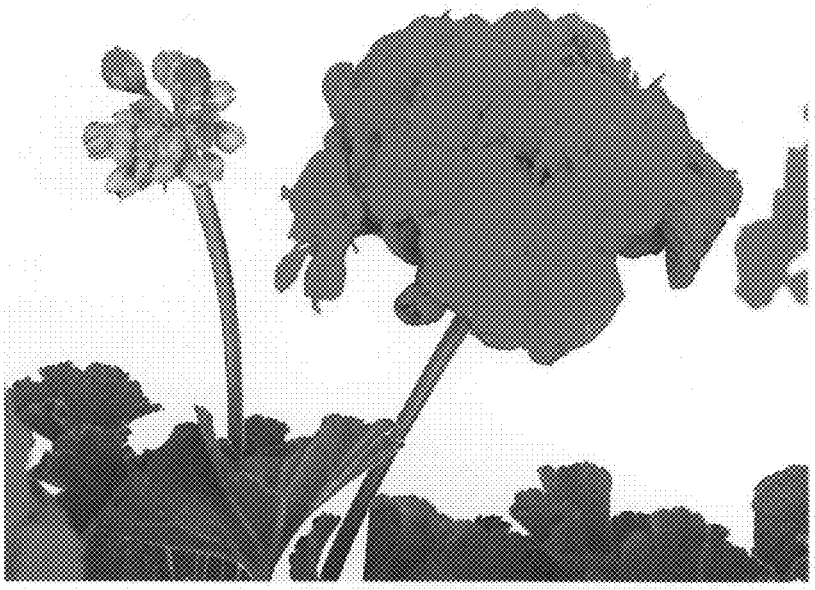
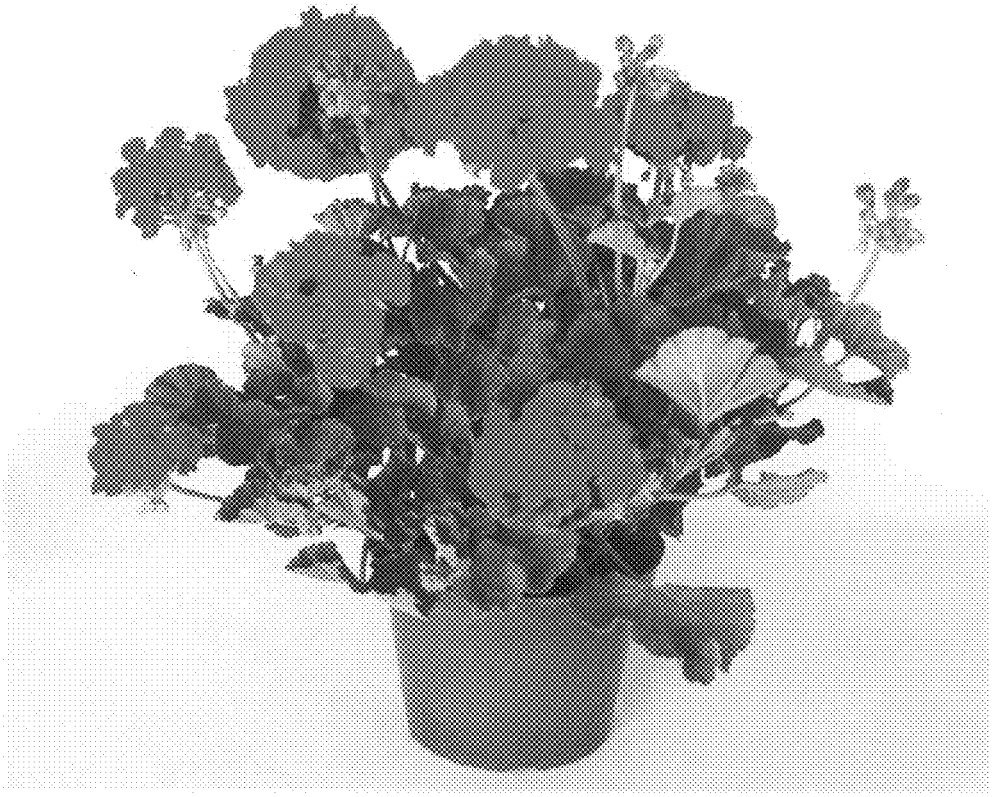

* * * * *